United States Patent
Teles et al.

Patent Number: 6,120,744
Date of Patent: *Sep. 19, 2000

[54] ADDITION REACTION OF HYDROXYl-CONTAINING COMPOUNDS WITH ALKYNES OR ALLENES

[75] Inventors: Joaquim Henrique Teles, Altrip; Norbert Rieber, Mannheim; Klaus Breuer, Altrip; Dirk Demuth, Mannheim; Hartmut Hibst, Schriesheim, all of Germany

[73] Assignee: BASF Aktiengesellschaft, Ludwigshafen, Germany

[*] Notice: This patent is subject to a terminal disclaimer.

[21] Appl. No.: 09/097,818

[22] Filed: Jun. 16, 1998

[30] Foreign Application Priority Data

Jun. 23, 1997 [DE] Germany .............................. 197 26 668

[51] Int. Cl.$^7$ .............................. C01G 9/00; C01G 11/00; C22B 13/00; C22B 17/00; C22B 43/00
[52] U.S. Cl. ............................ 423/99; 423/101; 423/109; 423/326; 423/327; 423/339
[58] Field of Search .............................. 423/99, 326, 327, 423/101, 109, 339

[56] References Cited

U.S. PATENT DOCUMENTS

| | | | |
|---|---|---|---|
| 3,954,937 | 5/1976 | Bodson .................................. | 423/101 |
| 4,681,749 | 7/1987 | Usui et al. .............................. | 423/326 |
| 5,342,876 | 8/1994 | Abe et al. .............................. | 524/493 |

FOREIGN PATENT DOCUMENTS

| | | |
|---|---|---|
| 265289 | 10/1985 | Germany . |
| 267629 | 10/1985 | Germany . |
| 239752 | 2/1942 | Switzerland . |

OTHER PUBLICATIONS

*Chem. Abst.*, vol. 112, No. 7, Feb. 12, 1990, AN 54986a (DD 267629).
*Chem. Abst.*, vol. 112, No. 7, Feb. 12, 1990, AN 54987b (DD 265289).
Houben–Weyl, Methoden der organischen chemie, vol. 6/3, pp. 233–239 and pp. 90–91.
Houben–Weyl, Methoden der organischen chemie, vol. 5/2a, pp. 738–740.
Houben–Weyl, Methoden der organischen chemie, vol. 6/1d, pp. 136–175.
Houben–Weyl, Methoden der organischen chemie, vol. 7/a, pp. 816–821.

*Primary Examiner*—James O. Wilson
*Attorney, Agent, or Firm*—Keil & Weinkauf

[57] ABSTRACT

A process for preparing compounds of the formulae I and II

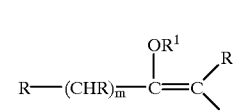

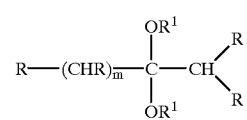

where $R^1$ and R have the meanings indicated in the specification by an addition reaction of a compound of the formula III $R^1OH$          III with an acetylene or allene of the formula IV or V

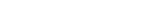

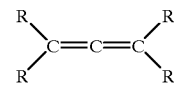

in the gas phase at elevated temperatures in the presence of a heterogeneous catalyst. The catalyst is obtained by impregnating silica with a zinc salt, by a process in which the reaction is carried out at below 200° C. and the catalyst contains, as an active component, an X-ray amorphous zinc silicate or cadmium silicate containing from 1 to 40% by weight, calculated as oxide, of zinc or cadmium, obtainable by applying a salt of zinc or cadmium and an inorganic oxo acid, which salt is decomposable at below 400° C., to amorphous silica and forming the catalyst before the reaction at from 50 to 500° C. or during the reaction in situ at from 50 to 200° C. in the presence of a hydroxyl-containing compound such as water, alkanols of 1 to 6 carbon atoms, diols and polyols having 2 to 6 carbon atoms and 2 or 3 OH groups and low molecular weight carboxylic acids.

10 Claims, 1 Drawing Sheet

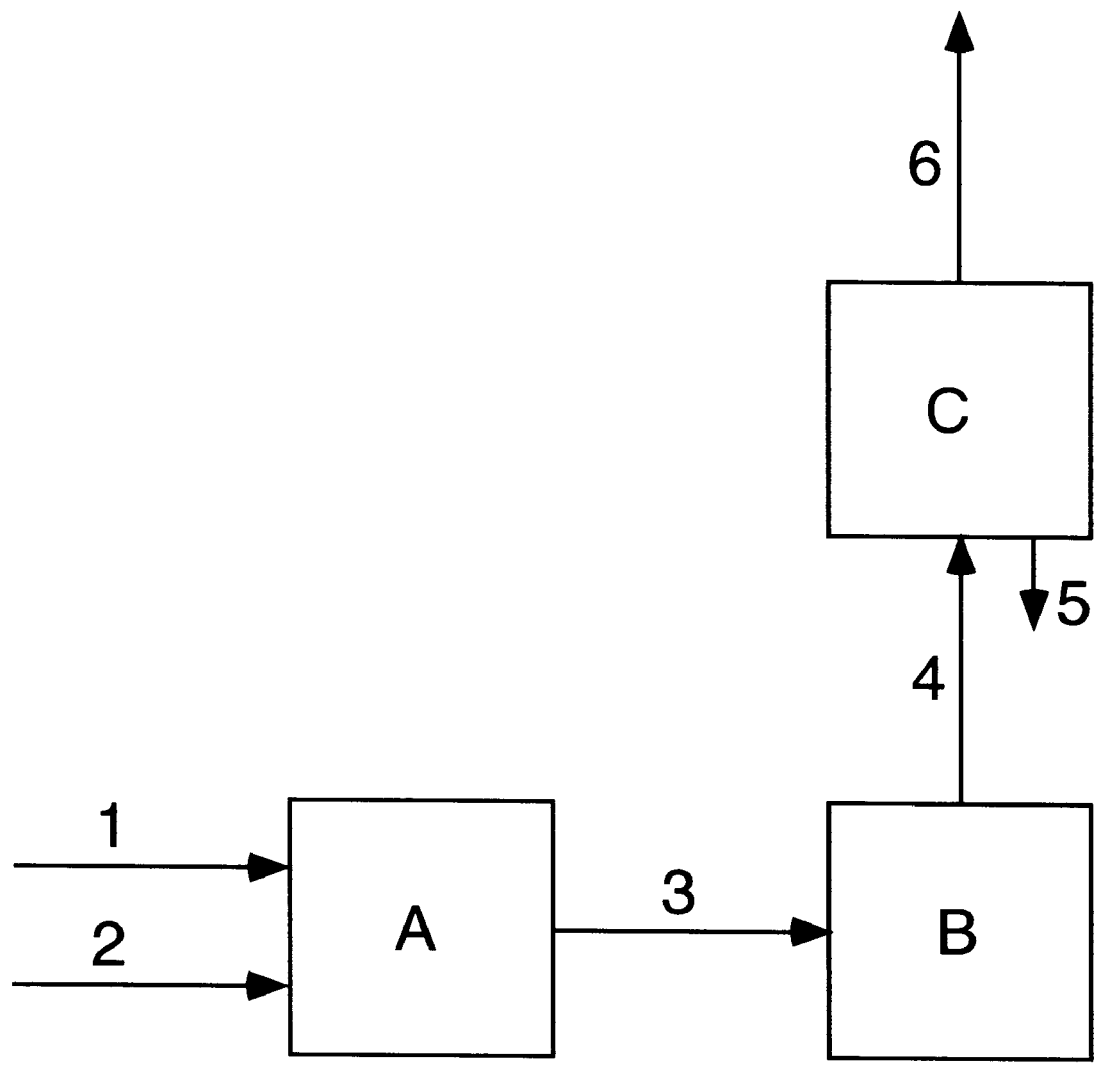

6,120,744

ADDITION REACTION OF HYDROXY1-CONTAINING COMPOUNDS WITH ALKYNES OR ALLENES

BACKGROUND OF THE INVENTION

1. Field of the Invention

The present invention relates to a process for the addition reaction of hydroxyl-containing compounds with alkynes or allenes with formation of aldehydes and ketones or derivatives thereof in the form of enol ethers or acetals or ketals in the presence of an amorphous zinc silicate or cadmium silicate catalyst. The present invention furthermore relates to a novel process for the preparation of a zinc silicate or cadmium silicate and to the catalyst thus obtained.

2. Description of the Related Art

The addition reaction of hydroxyl-containing compounds with alkynes or allenes is carried out virtually without exception using homogeneously dissolved catalysts, for example with acids, bases and transition metal complexes (cf. Houben-Weyl, Methoden der organischen Chemie, Vol. 6/3, page 233, page 90, Vol. 5/2a, page 738, Vol. 6/1d, page 136 and Vol. 7/a, page 816).

The acid catalysis is generally limited to the addition reaction with activated, electron-rich alkynes (such as acetylene ethers, $R-C \equiv C-OR'$, acetylene thioethers, $R-C \equiv C-SR'$, and acetylene amines, $R-C \equiv C-NR'_2$).

Under base catalysis (in the presence of KOH or alcoholate) alcohols can be subjected to an addition reaction in the liquid phase also with inactivated alkynes. This is the most common method; however, the reaction requires high temperatures and pressures and the space-time yield is relatively low. Typically, a residence time of from 6 to 10 hours at about 160° C. and from 18 to 20 bar are required for the base-catalyzed vinylation of an alcohol.

The addition reaction can also be catalyzed by transition metal complexes in the liquid phase. In particular, mercury (II) or gold(I) salts are suitable for the addition reaction of alcohols, while zinc and cadmium salts are preferred for the addition reaction of carboxylic acids and phenols.

The addition reaction of carboxylic acids (in particular acetic acid and propionic acid) with acetylene can also be carried out in the gas phase in the presence of, as catalysts, corresponding zinc carboxylates (including basic zinc carboxylates according to CH 239 752) on carriers having a large surface area.

Finally, the addition reaction of methanol with propyne or propadiene in the gas phase in the presence of zinc oxide on activated carbon or silica gel has also been described in DD 265 289 and that in the presence of zinc nitrate on activated carbon or silica gel in DD 267 629 at above 200° C.

All these prior art processes have disadvantages. They either have only limited application or, like the base-catalyzed addition reaction, require high pressures and temperatures, which may lead to safety problems, or they have only a low space-time yield. Homogeneously dissolved transition metal catalysts are often deactivated after a small number of cycles and in addition are difficult to recycle. Heterogeneous catalysts for the addition reaction with alkynes or allenes have only rarely been described to date. Zinc carboxylates or cadmium carboxylates on activated carbon catalyze only the addition reaction of carboxylic acids (eg. acetic acid or propionic acid) with acetylene. The abovementioned catalyst based on zinc oxide on activated carbon or silica gel (DD 265 289) is capable of catalyzing the addition reaction of alcohols (methanol or ethanol) with propyne or propadiene with good selectivity (from 90 to 96%), but the catalytic activity is relatively low, the required reaction temperatures are high and the necessary contact times are long, leading to rapid deactivation of the catalyst. Even at the temperature of above 200° C. used in DD 267 629, zinc nitrate on activated carbon or silica gel is about an order of magnitude less active than zinc oxide and the selectivity is much lower (max. 70%).

BRIEF SUMMARY OF THE INVENTION

The present invention to provides a heterogeneous catalyst which is very active and selective at low temperatures, ie. below 200° C., for the addition reaction of hydroxyl-containing compounds with alkynes, allenes or mixtures thereof.

DETAILED DESCRIPTION OF THE INVENTION

The invention is directed to a process for the preparation of compounds of the formulae I and II

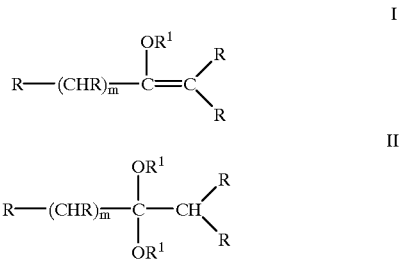

where $R^1$ is hydrogen or an aliphatic, cycloaliphatic, araliphatic, aromatic or heterocyclic radical or an acyl radical, it being possible for these radicals to carry further substituents which do not react with acetylenes or allenes, and the radicals R, independently of one another, are hydrogen or aliphatic, cyclo-aliphatic, araliphatic, aromatic or heterocyclic radicals which may be bonded to one another with the formation of a ring, and m is 0 or 1, by an addition reaction of a compound of the formula III $$R^1OH \qquad\qquad III$$

with an acetylene or an allene of the formula IV or V

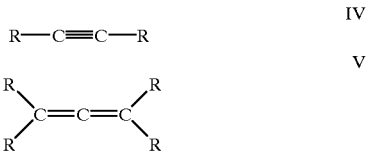

where $R^1$ and R have the abovementioned meanings, in the gas phase at elevated temperatures in the presence of a heterogeneous catalyst obtained by impregnating silica with an inorganic salt of an element of group 12 of the Periodic Table of Elements, wherein the reaction is carried out at below 200° C. and the catalyst used is one which contains, as an active component, an X-ray amorphous zinc silicate or cadmium silicate containing from 1 to 40% by weight, calculated as oxide, of zinc or cadmium and having, for example, a BET surface area of from 10 to 1000 $m^2/g$, obtainable by applying a salt of zinc or cadmium and an inorganic oxo acid, in particular nitric acid, which salt is decomposable at below 400° C., to amorphous silica and forming the catalyst before the reaction at from 50 to 500° C. or during the reaction in situ at from 50 to 200° C. in a gas/solid reaction in the presence of a hydroxyl-containing compound selected from the group consisting of water, alkanols of 1 to 6 carbon atoms, diols and polyols having 2 to 6 carbon atoms and 2 or 3 OH groups and carboxylic acids of 1 to 6 carbon atoms.

The catalysts to be used according to the invention may furthermore be doped with up to 80, preferably up to 20, mol percent of other metals selected from the group (A) consisting of sodium, potassium, lithium, cesium, beryllium, magnesium, calcium, strontium, barium, manganese, iron, cobalt, nickel and copper and from the group (B) consisting of titanium, zirconium, hafnium, germanium, tin and lead.

In a preferred embodiment of the process, amorphous zinc silicate is used and 2-methoxypropene is prepared by an addition reaction of methanol with propyne and/or allene.

Suitable starting materials for the novel reaction are any desired alkynes or allenes or mixtures thereof. As a rule, however, industrially readily obtainable acetylenes and allenes of 2 to 8 carbon atoms and 3 to 8 carbon atoms, respectively, are used.

The hydroxyl-containing compound $R^1OH$ may be water, any desired alcohol, a phenol or a carboxylic acid. Especially alcohols, in particular alkanols of 1 to 16 carbon atoms, mononuclear phenols and low molecular weight carboxylic acids, for example of 1 to 16 carbon atoms, are generally suitable.

The alkanol used for forming the catalyst is advantageously the same alkanol ($R^1OH$) as that subjected to the addition reaction with the acetylene or allene.

The addition reaction of the hydroxyl-containing compounds is carried out in the presence of the heterogeneous catalyst present in the gas phase, either over a fixed bed or in a fluidized bed, at from 50 to 200° C., preferably from 100 to 200° C., particularly preferably from 120 to 200° C. and from 0.1 to 100, in particular from 0.8 to 20, bar (all pressures are based on the sum of the partial pressures of the starting materials).

For reasons of operational safety and better heat removal, the reaction mixture can, if required, be diluted with inert gases, such as nitrogen, argon, low molecular weight alkanes or olefins.

The molar ratio of the hydroxyl-containing component to alkyne or allene may be from 0.01 to 100, preferably from 0.1 to 5, particularly preferably from 0.7 to 1.3.

The selectivity of the reaction with respect to the monoadducts and diadducts can be controlled by means of the reaction conditions. Low ratios of the hydroxyl-containing component to alkyne or allene and high temperatures and low partial pressures of the reactants lead to preferential formation of the monoadducts, whereas high ratios of the hydroxyl-containing component to alkyne or allene and low temperatures and high partial pressures of the reactants promote the formation of the bisadducts. For example, depending on the reaction conditions, 2-methoxypropene or 2,2-dimethoxypropane can be formed selectively from propyne or allene using methanol

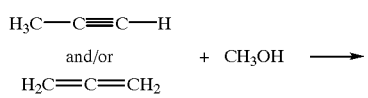

+ CH$_3$OH ⟶

-continued

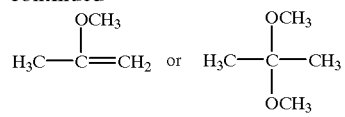

For the preparation of the catalyst, the amorphous SiO$_2$ carrier is impregnated with a solution, advantageously an aqueous solution, of the zinc or cadmium nitrates. Mixing of the dry nitrates or nitrates suspended in the alcohols $R^1OH$ with the carrier is possible but not advantageous.

The SiO$_2$ carrier is at least substantially amorphous, has a BET surface area of from 10 to 1500, preferably from 100 to 500, m$^2$/g and a water absorptivity of from 0.1 to 2, preferably from 0.7 to 1.3, ml/g and can be used in the form of a powder or as prepared molding. The carrier may also be calcined before impregnation. However, the carrier is preferably not calcined.

Among the inorganic salts to be applied, the nitrates are preferred, in particular zinc nitrate being preferable to cadmium nitrate.

The impregnation is effected by catalyst preparation methods known per se. If required for solubility reasons, the loading with the active metal may also be carried out in a plurality of successive impregnation steps.

If the carrier is used in the form of a powder, it can be brought to the desired shape prior to forming by shaping (for example by mixing, kneading and extruding or pelleting).

In order to increase the pore volume, pore formers (eg. superabsorbers such as Lutexal P® (from BASF AG) or Walocel® (methylcellulose/synthetic resin combination, from Wolff, Walsrode AG)) may also be added during the shaping procedure.

Alternatively, it is also possible to impregnate another carrier, eg. Al$_2$O$_3$, together with a silica precursor compound (eg. Si(OR)$_4$) and with a zinc salt.

The zinc or cadmium loading can be varied within wide limits, for example from 1 to 40% by weight, calculated as oxides. Zinc or cadmium contents of from 7 to 30% by weight are preferred, particularly preferably from 10 to 25% by weight. The resulting precatalyst which is still not active can then be calcined at not more than 600° C. in air or under inert gas. Calcination temperatures of from 80 to 300° C. are preferred. Calcination at from 120 to 250° C. in air is particularly preferred. In the calcination, it is advantageous to choose the temperature and residence time so that the molar ratio of the anion still present to zinc or cadmium does not fall below 0.1

After the preparation of the precatalyst, formation, in which the actual active phase preferably forms on the surface of the catalyst, is carried out before introduction into the reactor or in situ in the reactor. This gas/solid reaction is promoted at from 80 to 500° C. by the presence of water, alcohols, preferably lower alcohols, or carboxylic acids, preferably lower carboxylic acids. The formation of the catalyst is preferably carried out at from 100 to 250° C. in a water- or methanol-containing gas mixture and particularly preferably from 130 to 200° C. with a methanol-containing gas mixture in situ in the reactor in which the reaction with the alkyne or allene takes place. Advantageously, for the formation of the active phase, the precatalyst is reacted under reaction conditions with a mixture of methanol and propyne and allene and, if required, also other inert components, eg. propene or propane. The formation of the active layer is indicated by the increase in the propyne and allene conversion (after from about 5 to 30 minutes, depending on the temperature) and by the decline in the concentration of methyl acetate in the exit gas. Steady state and high selectivity are achieved after from about 2 to 20 hours, depending on the temperature.

Standard methods were used for characterizing the catalyst samples (fresh samples as well as samples removed from the reactor). The measured BET surface area (as a rule from 10 to 800 m$^2$/g) and the hardness are stated in the respective example. Catalysts having BET surface areas of from 100 to 400 m$^2$/g are preferably used. Furthermore, the samples were thoroughly investigated by means of powder X-ray diffractometry (XRD) and transmission electron microscopy (TEM). Neither of the structure analysis methods indicates any long-range order in the sense of a crystalline structure, and all samples were amorphous. The distribution of the zinc over the carrier was investigated using sections under the electron microscope and with a microprobe. After removal from the reactor, all samples showed that the catalyst has a substantially homogeneous distribution of elements and contains little or no crystalline ZnO. In the $^{29}$Si-CP-MAS-NMR, the catalyst showed only the broad band at −109 ppm, typical of amorphous SiO$_2$, and a shoulder at −99 ppm (about 15% of the intensity of the main peak). Elemental analysis of a zinc nitrate/SiO$_2$ precatalyst showed that the molar nitrate/Zn ratio is dependent on the calcination temperature. Catalysts dried at room temperature have a nitrate/Zn ratio of 1.6–1.9. After calcination at 120° C., the nitrate/Zn ratio is from 1.0 to 1.5. After calcination in the preferred temperature range of from 200 to 250° C., the nitrate/Zn ratio is from 0.5 to 1. At higher temperatures, the nitrate/Zn ratio decreases even further, as does the catalytic activity of the catalysts formed therefrom.

For the reaction, the catalyst can be arranged as a fixed bed or, for example, also used in a fluidized bed and may have an appropriate shape for this purpose, for example chips, pellets, monoliths, beads or extrudates (extrudates having cross-sections such as solid extrudates, waggon wheels, stars or rings).

a) General reaction conditions

The catalytic reactions according to FIG. 1 were carried out in a gradient-free CSTR (Continuously Stirred-Tank Reactor) (A) having a volume of 1740 ml and a catalyst volume of about 90 ml, modified for heterogeneous gas-phase reactions. The reactor had an internal diameter of about 108 mm and a height of about 200 mm and was heated by means of an electrical heating coil mounted on the inner surface. A small metal cylinder (Ø about 64 mm, height about 150 mm) was mounted in the center of the reactor and was provided with a wire grid at half height (about 85 mm below the upper edge). The catalyst was poured loosely onto this wire grid. A flat turbine (Ø about 100 mm, height about 20 mm) was mounted on the reactor cover and driven at 1500–2000 rpm. A total of 6 thermocouples for temperature monitoring were mounted at different heights along the reactor axis. The starting materials were metered under pressure by means of HPLC pumps, mixed shortly before the reactor and let down into the reactor space. The alkyne or allene (1 in FIG. 1) was metered in either in pure form or as a mixture diluted with other inert components. In the case of propyne and allene, a mixture with other hydrocarbons was used (composition: 30–43% by volume of propyne, 16–20% by volume of allene, 20–45% by volume of propene, 5–10% by volume of isobutane and 2–6% by volume of propane as main components; all other components less than 1%. This mixture was obtained by distillation from a side stream of a steam cracker). About 10% by weight of cyclohexane, as an internal standard for the GC analysis, were metered into the alcohol component (2 in FIG. 1).

The reaction was carried out isothermally at from 120 to 200° C. and at a feed rate of from 0.5 to 10 mmol/min of propyne and/or allene and from 0.5 to 20 mmol/min of methanol. The reaction pressure was from 1.1 to 3.5 bar (absolute).

The total amount of gas, consisting of starting materials, inert gas and internal standard, was as a rule from 4 to 60 l (S.T.P.)/h. The GHSV (gas hourly space velocity), which is defined as GHSV=gas volume [1(S.T.P.)/h]/catalyst volume [1], was from 80 to 1200 h$^{-1}$. The LHSV (liquid hourly space velocity), which is defined as LHSV=liquid volume [1(S.T.P.)/h]/catalyst volume [1] (in this case the transported volume of propyne and the volume of methanol), was from 0.2 to 3 h$^{-1}$. The residence time, defined as the quotient of the catalyst volume [1] and the amount of gas [1(S.T.P.)/s] was from 3 to 40 s.

After leaving the reactor, the reaction gases were passed via a heated transfer line (3) to an on-line gas chromatograph (B) and analyzed there every 2 hours. Thereafter, the gas stream was subjected to partial condensation (C) and the fraction (6) not condensable at room temperature was analyzed at regular intervals (about 12 hours) by means of off-line GC. The condensate (5) was likewise collected and was analyzed by means of off-line GC.

Unless stated otherwise, the conversions and selectivities are based on the sum of propyne and allene.

b) Methods for characterizing the catalysts

Standard methods were used for characterizing the catalyst samples (fresh samples as well as samples removed from the reactor). The measured BET surface area and the hardness are stated in the respective example. Furthermore, the samples were thoroughly analyzed by means of powder X-ray diffractometry (XRD) and transmission electron microscopy (TEM). The distribution of the zinc over the carrier was monitored by means of sectional images under the electron microscope and by means of a microprobe.

Selected samples were furthermore analyzed by means of IR, $^{29}$Si-CP-MAS-NMR and EXAFS.

The enol ethers of the formula I which are obtainable according to the invention and the dialkoxy compounds of the formula II are useful intermediates for the preparation of active ingredients and fragrances. In particular, the enol ethers are desirable starting materials, for example for the preparation of γ, δ-unsaturated ketones as intermediates for the preparation of isophytol.

If it is intended to obtain in particular the enol ethers, the compounds of the formula II can be converted into the corresponding enol ethers of the formula I in a manner known per se by eliminating one mole of R$^1$OH. A large number of processes disclosed in DE-A-35 35 128, DE-A-37 22 891, DE-A-38 04 162, Chemical Abstracts, Vol. 94 (19); 156241f and DE-A-19544450 exist for this purpose.

Examples 1 to 3

Impregnation with zinc nitrate (20% of ZnO, 80% of SiO$_2$)

An impregnation solution consisting of 365.52 g of Zn(NO$_3$)$_2$.6H$_2$O (Merck) dissolved in 480 g of distilled water was divided into two 340 ml portions and 400 g of SiO$_2$ carrier (Siligel, from Solvay) were impregnated with the first portion at room temperature and the precatalyst was then dried for 16 hours at 120° C. and impregnated with the second portion at room temperature. The still moist precatalyst was then divided into three portions, which were calcined under various conditions (cf. Table 1). The molar NO$_3$/Zn ratio in the precatalyst is likewise shown in Table 1.

About 90 ml of the respective precatalyst were introduced into the apparatus described above. Propyne/allene mixture (about 52% strength by volume, 2.9 mmol/min) and methanol (2.1 mmol/min; total feed with inert substances: 7.8 mmol/min; methanol/(propyne+allene) ratio=0.71) were then metered in by means of HPLC pumps. The reaction temperature was 170° C. and the pressure 1.2 bar (absolute, partial pressure of the starting materials: 0.77 bar). After formation of the catalyst was complete (about 14 hours), the selectivities shown in Table 1 were observed (Abbreviations: 2 MP: 2-methoxypropene; 2 DMP: 2,2-dimethoxypropane; 1 MP: cis-and trans-1-methoxypropene; 1DMP: 1,1-dimethoxypropane).

TABLE 1

| # | Calcination T/° C. | Calcination Time/h | Pre-catalyst NO$_3$/Zn | 2MP | 2DMP | Selectivities Acetone | 1MP | 1DMP | Conversion Propyne/allene |
|---|---|---|---|---|---|---|---|---|---|
| 1 | 120 | 16 | 0.33 | 81% | 10% | 2% | 5% | 1% | 37% |
| 2 | 250 | 4 | 0.61 | 83% | 9% | 1% | 5% | 1% | 39% |
| 3 | 320 | 2 | 0.17 | 83% | 8% | 1% | 6% | 1% | 27% |

The following values were determined for the completely formed catalyst after removal from the reactor: BET surface area 180–210 m$^2$/g, hardness 40–65 N/molding. The NO$_3$/Zn ratio was always <0.05 in the catalysts removed from the reactor.

Example 4

Impregnation with zinc perchlorate (20% of ZnO, 80% of SiO$_2$)

The Zn/SiO$_2$ supported catalyst was prepared by impregnating X-ray amorphous SiO$_2$ moldings (beads of 3–6 mm Ø) having a BET surface area of 358 m$^2$/g, a water absorptivity of 0.9 ml/g and a hardness of 43 N/molding with zinc perchlorate solution.

100 g of SiO$_2$ carrier (Siligel, from Solvay) were impregnated with 114.4 g of Zn(ClO$_4$)$_2$·6$^H_2$O (Aldrich) dissolved in 30 g of water at room temperature and the precatalyst was then dried for 16 hours at 120° C. and then calcined for 4 hours at 250° C. under air.

About 90 ml of the precatalyst were introduced into the apparatus described above. Propyne/allene mixture (about 52% strength by volume, 2.9 mmol/min) and methanol (2.1 mmol/min; total feed with inert substances: 7.8 mmol/min; methanol/(propyne+allene) ratio=0.71) were then metered in by means of HPLC pumps. The reaction temperature was 170° C. and the pressure 1.2 bar (absolute) and the partial pressure of the starting materials was 0.77 bar. After formation of the catalyst was complete (about 14 hours) the propyne/allene conversion was 23%. The main products formed (selectivities with respect to propyne+allene in brackets) were 2-methoxypropene (79%), 2,2-dimethoxypropane (10%), 1-methoxypropene (6%) and acetone (3%).

We claim:

1. A process for the preparation of compounds of the formulae I and II

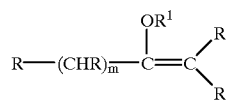

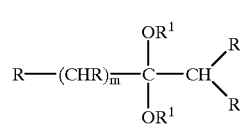

where R$^1$ is hydrogen or an aliphatic, cycloaliphatic, araliphatic, aromatic or heterocyclic radical or an acyl radical, it being possible for these radicals to carry further substituents which do not react with acetylenes or allenes, and the radicals R, independently of one another, are hydrogen or aliphatic, cycloaliphatic, araliphatic, aromatic or heterocyclic radicals which may be bonded to one another with the formation of a ring, and m is 0 or 1, by an addition reaction of a compound of the formula III

R$^1$OH     III with an acetylene or an allene of the formula IV or V

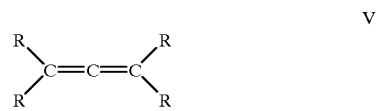

where R$^1$ and R have the abovementioned meanings, in the gas phase at elevated temperatures in the presence of a heterogeneous catalyst obtained by impregnating silica with an inorganic salt of an element of group 12 of the Periodic Table of Elements, wherein the reaction is carried out at below 200° C. and the catalyst used is one which contains, as an active component, an X-ray amorphous zinc silicate or cadmium silicate containing from 1 to 40% by weight, calculated as oxide, of zinc or cadmium, obtainable by applying a salt of zinc or cadmium and an inorganic oxo acid, which salt is decomposable at below 400° C., to amorphous silica and forming the catalyst before the reaction at from 50 to 500° C. or during the reaction in situ at from 50 to 200° C. in the presence of a hydroxyl-containing compound selected from the group consisting of water, alkanols of 1 to 6 carbon atoms, diols and polyols having 2 to 6 carbon atoms and 2 or 3 OH groups and carboxylic acids of 1 to 6 carbon atoms.

2. A process as claimed in claim 1, wherein the catalyst used is one whose catalytically active component is furthermore doped with up to 80 mol percent, based on zinc or cadmium, of further metals selected from the group (A)

consisting of sodium, potassium, lithium, rubidium, cesium, beryllium, magnesium, calcium, strontium, barium, manganese, iron, cobalt, nickel and copper, and from the group (B) consisting of titanium, zirconium, hafnium, germanium, tin and lead.

3. A process as claimed in claim 1, wherein the catalyst used is one which was formed in the presence of the same alkanol which is to be reacted with the acetylene or allene.

4. A process as claimed in claim 1, wherein the catalyst used is one which is obtainable by impregnation of amorphous silica with zinc nitrate in aqueous solution and subsequent formation.

5. A process as claimed in claim 1, wherein the addition reaction of the hydroxyl-containing compound $R^1OH$ with the compounds of the formulae IV and V is carried out at from 100 to 200° C.

6. A process as claimed in claim 1, wherein 2-methoxypropene or 2,2-dimethoxypropane is prepared by an addition reaction of methanol with methylacetylene or allene at from 100 to 200° C.

7. A process for the preparation of an X-ray amorphous zinc silicate or cadmium silicate suitable for the process as claimed in claim 1, wherein salts of zinc or cadmium and an inorganic oxo acid which are decomposable at below 400° C. are applied to amorphous silica by dry blending or impregnation with a solution of the salts, and the catalyst is formed in the presence of hydroxyl-containing compounds in a gas/solid reaction at from 50 to 500° C.

8. A process as claimed in claim 7, wherein, before the formation of the catalyst by the gas/solid reaction at from 50 to 500° C., the precatalyst obtained by applying the zinc or cadmium salt to the amorphous silica is subjected to a calcination at from 100 to 400° C., the temperature and the residence time being chosen so that the precatalyst still contains at least 10 mol% of the original anion of the salts.

9. A process as claimed in claim 7, wherein an amorphous zinc silicate is obtained by impregnation of amorphous silica with a zinc-nitrate solution and subsequent formation.

10. An X-ray amorphous zinc silicate or cadmium silicate catalyst as obtained by the process of claim 7, which contains from 1 to 40% by weight, calculated as oxide, of zinc or cadmium.

* * * * *